United States Patent [19]

Horodysky et al.

[11] 4,368,129
[45] Jan. 11, 1983

[54] MULTIFUNCTIONAL LUBRICANT ADDITIVES AND COMPOSITIONS THEREOF

[75] Inventors: Andrew G. Horodysky, Cherry Hill; Joan M. Kaminski, Clementon, both of N.J.

[73] Assignee: Mobil Oil Corporation, New York, N.Y.

[21] Appl. No.: 259,217

[22] Filed: Apr. 30, 1981

[51] Int. Cl.$^3$ .................... C10M 1/46; C07F 5/02; C07F 9/02
[52] U.S. Cl. .................... 252/32.7 E; 252/389 A; 252/400 A; 260/429 R; 260/429.9; 260/430; 260/439 R
[58] Field of Search .......... 252/32.7 E, 389 A, 400 A; 260/429.9, 429 R, 430, 439 R

[56] References Cited

U.S. PATENT DOCUMENTS 2,344,392  3/1944  Cook et al. .................... 252/32.7 E
3,288,819  11/1966  Tichelaar et al. .............. 252/32.7 E
4,148,738  4/1979  Liston et al. .................... 252/32.7 E

*Primary Examiner*—W. J. Shine
*Attorney, Agent, or Firm*—Charles A. Huggett; Michael G. Gilman; Howard M. Flournoy

[57] ABSTRACT

Metal salts of partially borated, partially phosphosulfurized polyols and hydroxyl-containing esters are effective multifunctional friction reducing, antioxidant and copper strip passivating additives when used in lubricating media.

15 Claims, No Drawings

MULTIFUNCTIONAL LUBRICANT ADDITIVES AND COMPOSITIONS THEREOF

BACKGROUND OF THE INVENTION

1. Field of the Invention

This invention is directed to multifunctional lubricant additives particularly useful as friction modifiers, oxidation inhibitors and copper-strip passivators, to compositions containing same and to a means of increasing the fuel consumption of internal combustion or turbine engines. In a more particular aspect this invention is directed to metal salts of partially borated, partially phosphosulfurized hydroxyl-containing esters derived from polyols and to lubricating fluids containing said borated phosphosulfurized metal salts.

2. Discussion of Prior Art

The metal surfaces of machinery or engines operating under heavy loads wherein metal slides against metal may undergo excessive wear or corrosion. Often, the lubricants used to protect the metal surfaces deteriorate under such heavy loads and as a result, do not prevent wear at the points of metal to metal contact. Consequently, the performance of the machine or engine will suffer, and in aggravated cases the machine or engine may become completely inoperative.

It is also known that lubricants are prone to oxidative deterioration when subjected to elevated temperatures or even when they are exposed to atmospheric conditions for long periods of time. Such deterioration of lubricants, including lubricating oils and greases, produces loss of lubricating properties of the oil, grease or other lubricant subjected to oxidation.

Accordingly, there is a need for a multifunctional additive system capable of effectively reducing wear, inhibiting corrosion and reducing oxidative deterioration. There have been many attempts to devise additive systems which would provide satisfactory protection in imparting friction reducing, antioxidant and anticorrosion properties to lubricants. Many prior art additives have, however, been only marginally effective in accomplishing such objective except at unacceptably high concentrations, especially when the lubricants are subjected to drastic oxidizing conditions.

U.S. Pat. No. 3,652,410 describes multifunctional lubricant additive compositions comprising overbased metal salts and sulfur-containing compounds. U.S. Pat. No. 4,162,224 describes antiwear and antioxidant additive compounds comprising certain borates of bisoxazolines. However, no art known to applicants discloses or suggests the use of metal salts of partially borated, partially phosphosulfurized hydroxyl-containing esters derived from polyols as multifunctional lubricant additives.

SUMMARY OF THE INVENTION

In accordance with the present invention certain metal salts of partially borated, partially phosphosulfurized hydroxyl-containing esters derived from polyols significantly reduce friction when incorporated into lubricating fluids. These novel additive compounds concomitantly reduce engine wear and inhibit bearing corrosion when used in, for example, internal conbustion engine lubricants.

The novel compounds of the present invention as stated hereinabove are metal salts of partially phosphosulfurized and partially borated hydroxyesters derived from polyols. Zinc is the preferred metal although other metals such as nickel, iron, cobalt, silver and molybdenum can also be used. Lubricant compositions containing these metal salts are substantially improved with respect to antioxidant, antiwear and anticorrosion properties as well as exhibiting significant friction reducing properties. The hydroxyesters of the present invention contain both boron and phosphorodithioate linkages combining the advantages provided by both of these individual moieties in one composition having far superior characteristics to those provided by mere mixtures of borated and phosphosulfurized hydroxyesters. It is believed that the boron in the partially borated, partially phosphosulfurized hydroesters provides the enhanced friction reduction and antioxidation, and that the P-S bonds in these molecules provide the antiwear/antioxidation and bearing corrosion inhibiting properties. The data set forth hereinbelow clearly show the multifunctional and/or synergistic contribution of the various elements of this invention.

The additive compounds of the instant invention may be conveniently prepared by first partially phosphosulfurizing a hydroxyl-containing ester by reacting the hydroxyl-containing ester with a phosphosulfur compound such as phosphorus pentasulfide and then reacting the partially phosphosulfurized compound, for example, partially phosphosulfurized glycerol monooleate with a metal compound such as zinc oxide and thereafter borating the metal salt of the partially phosphosulfurized hydroxyl-containing ester in any convenient manner known to the art. The hydroxyl-containing ester such as glycol monooleate is partially phosphosulfurized by reacting with a phosphosulfur compound such as phosphorus pentasulfide in a suitable solvent, such as benzene, toluene, xylene, or neat at a temperature between about 70° C. and about 110° C. employing a molar ratio of hydroxy-containing ester to phosphorus pentasulfide of between about 1:1 to about 8:1.

The metal salt of the partially phosphosulfurized compound may then be reacted directly with boric acid or a suitable boron compound including for example, trialkyl borates such as trimethyl borate, triethyl borate or tributyl borate. Reaction is usually effected at a temperature between about 70° C. and about 150° C. employing a molar ratio of the partially phosphosulfurized metal salt to the boric acid or other boron compound of between about 1:1 to about 6:1.

Alternatively, the additive compounds of this invention can also be prepared by (3) borating the partially phosphosulfurized hydroxy-containing ester as described and (2) then reacting the borated partially phosphosulfurized compounds with a metal salt.

Another possible method of synthesizing the novel additives of this invention includes partially reacting the hydroxyl-containing ester with a boron containing compound, then partially phosphosulfurizing the intermediate, and thereafter reacting it with a metal compound. Mixtures of hydroxy esters can also be used. Partially is meant to include less than molar or less than equivalent amounts.

The hydroxyl-containing polyol-derived esters may be obtained commercially or prepared in any convenient manner known in the art. These hydroxyl-containing compounds can be depicted as

-continued

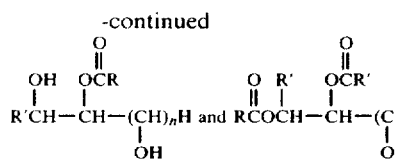

where R=$C_8$–$C_{30}$, and is saturated or unsaturated, straight chain or branched, cyclic hydrocarbyl, alkylaryl, arylalkyl; R' and R'' can be H or $C_1$–$C_{10}$ hydrocarbyl and n=1 to 4.

Examples include mono and dihydroxyl-containing esters made by reacting polyols such as glycerol, sorbitol, and sorbitan with acids such as lauric, myristic, palmitic, stearic, oleic, linoleic, and linolenic or mixtures of these. Consequently, suitable hydroyesters include mono- or di-esters of glycerol, sorbitol, sorbitan, butane triols, longer chain alkyl polyols, etc. and mixtures thereof.

The above-described novel partially phosphosulfurized, partially borated hydroxyl-containing polyol-derived esters can be incorporated into any suitable lubricating media. Suitable lubricating media comprise oils of lubricating viscosity, mineral or synthetic; or mixtures of mineral and synthetic oils and/or various functional oil base fluids or solid lubricants or greases in which any of the aforementioned oils may be employed as the vehicle. Such functional fluids include hydraulic oils, brake oils, power transmission oils and the like.

In general, where mineral oils are employed as the lubricant, or grease vehicle they may be of any suitable lubricating viscosity, as for example ranging from about 45 SSU at 100° F. to about 6000 SSU at 100° F., and, preferably, from about 50 to about 250 SSU at 210° F. These oils may have viscosity indices from below zero to about 100 or higher. Viscosity indices from about 70 to about 95 are preferred. The average molecular weight of these oils may range from about 250 to about 800. Where the lubricant is to be employed in the form of a grease, the mineral and/or synthetic lubricating oil is generally employed in an amount sufficient to balance the total grease composition, after accounting for the desired quanity of the thickening agent and other additive components to be included in the grease formulation.

In instances where synthetic oils are the lubricant, or where synthetic oils are employed as the vehicle for a grease or other solid lubricants in preference to mineral oils, or in combination therewith, various synthetic compounds may be successfully utilized. Typical synthetic oils or vehicles include polyisobutylene, polybutenes, hydrogenated polydecenes, polypropylene glycol, polyethylene glycol, trimethylol propane esters, neopentyl and pentaerythritol esters, di(2-ethyl hexyl) sebacate, di(2-ethyl hexyl) adipate, dibutyl phthalate, fluorocarbons, silicate esters, silanes, esters of phosphorous-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxy phenyl) ether, phenoxy phenylethers, etc.

As hereinbefore indicated, the aforementioned additive compounds may also be incorporated as inter alia antiwear agents in grease compositions. When high temperature stability is not a requirement of the finished grease, mineral oils having a viscosity of at least 40 SSU at 150° F., and particularly those falling within the range from about 60 SSU to about 6,000 SSU at 100° F. may be employed. The lubricating vehicles of the improved greases of the present invention, containing the above-described additives, are combined with a grease-forming quantity of a thickening agent. For this purpose, a wide variety of materials dispersed in the lubricating vehicle in grease-forming quantities in such degree as to impart to the resulting grease composition the desired consistency. Exemplary of the thickening agents that may be employed in the grease formulation are non-soap thickners, such as surface-modified clays and silicas, uryl ureas, calcium complexes and similar materials. In general, grease thickners may be employed which do not melt and dissolve when used at the required temperature within a particular environment; however, in all other respects, any material which is normally employed for thickening or gelling hydrocarbon fluids or forming greases can be used in preparing the aforementioned improved greases in accordance with the present invention. The fully formulated lubricant may include a variety of dispersants, detergents, inhibitors, antioxidants, pour depressants, antiwear, antifoam, and/or other additives for their intended purposes.

DESCRIPTION OF SPECIFIC EMBODIMENTS

The following examples will serve to illustrate the additive compounds and lubricant compositions of the invention without limiting same.

EXAMPLE 1

Glycerol Monooleate

Obtained commercially as a 60:40 mixture of mono and dioleates, respectively.

EXAMPLE 2

Partially Phosphosulfurized Glycerol Monooleate (GMO) (4 Moles GMO: 1 Mole $P_2S_5$)

Approximately 2000 grams of glycerol monooleate were charged to a reaction flask equipped with a stirrer, thermometer, condenser, and caustic scrubber. Approximately 200 grams toluene were added and the mixture was heated to about 80° C. Over a period of one hour, 240 grams of phosphorus pentasulfide were added. The reaction mixture was held at 90° C. for 4 additional hours at which time no further $H_2S$ evolution was observed Toluene was removed by vacuum distillation, and the product residue filtered. The resulting partially phosphosulfurized glycerol monooleate was a clear amber liquid.

EXAMPLE 3

Zinc Salt of Partially Phosphosulfurized Glycerol Monooleate

Approximately 300 grams of the partially phosphosulfurized ester prepared as described in Example 2 and 52.5 grams zinc oxide were refluxed at 95° C. for 4 hours in 180 grams of toluene and 18 grams isopropanol as solvents. The solvents were removed by vacuum distillation. The product was filtered through diatomaceous earth to yield a clear amber fluid containing:
1.83% phosphorus
3.9% sulfur
6.7% zinc

EXAMPLE 4

Partially Borated Zinc Salt of Partially Phosphosulfurized Glycerol Monooleate Approximately 100 grams of the zinc salt of partially phosphosulfurized glycerol monooleate, prepared as described in Example 3, were reacted with 4 grams of boric acid in 60 grams of toluene solvent. The reaction solution was refluxed from 100° to 125° C. until water no longer azeotroped from the reaction (3.2 cc $H_2O$). Toluene was removed by vacuum distillation, and the product residue was filtered through diatomaceous earth to yield a clear amber liquid.

EXAMPLE 5

Zinc Salt of Partially Borated, Partially Phosphosulfurized Glycerol Monooleate Approximately 100 grams of partially phosphosulfurized glycerol monooleate, prepared as described in Example 2, was reacted with 4 grams of boric acid in 60 grams toluene solvent. The reaction solution was refluxed from 100° to 125° C. until water no longer azeotroped from the reaction (3.1 cc $H_2O$). The product mixture was filtered through diatomaceous earth to yield a clear amber fluid. This toluene solution of partially borated, partially phosphosulfurized glycerol monooleate was refluxed with 18 grams zinc oxide in 3 grams isopropanol at 95° C. for 4 hours. Solvents were removed by vacuum distillation, and the product was filtered through diatomaceous earth to yield a clear amber fluid.

EXAMPLE 6

Partially Phosphosulfurized Glycerol Monooleate (GMO) 6 Moles GMO: 1 Mole $P_2S_5$)

Approximately 2000 grams of glycerol monooleate were charged to a reaction flask equipped with a stirrer, thermometer, condenser, and caustic scrubber. Approximately 200 grams toluene were added and the mixture was heated to about 80° C. Over a period of one hour, 160 grams of phosphorus pentasulfide were added. The reaction mixture was held at 90° C. for 4 additional hours at which time no further $H_2S$ evolution was observed. Toluene was removed by vacuum distillation, and the product residue was filtered through filter paper. The resulting partially phosphosulfurized glycerol monooleate was a clear, amber fluid.

EXAMPLE 7

Zinc Salt of Partially Phosphosulfurized Glycerol Monooleate

Approximately 300 grams of the above partially phosphosulfurized ester prepared as in Example 6 and 52.5 grams zinc oxide were refluxed at 95° C. for 4 hours in 180 grams toluene and 18 grams isopropanol as solvents. The solvents were removed by vacuum distillation. The product was filtered through diatomaceous earth to yield a clear amber fluid containing:

1.15% phosphorus
2.7% sulfur
4.4% zinc

EXAMPLE 8

Partially Borated Zinc Salt of Partially Phosphosulfurized Glycerol Monooleate Approximately 100 grams of the zinc salt of partially phosphosulfurized glycerol monooleate, prepared as described in Example 7, were reacted with 8 grams boric acid in 60 grams of toluene solvent. The reaction solution was refluxed from 100° to 124° C. until water no longer azeotroped from the reaction (5.2 cc $H_2O$). Toluene was removed by vacuum distillation, and the product residue was filtered through diatomaceous earth to yield a clear amber liquid.

EXAMPLE 9

Zinc Salt of Partially Borated, Partially Phosphosulfurized Glycerol Monooleate Approximately 100 grams of partially phosphosulfurized glycerol monooleate, prepared as described in Example 6, were reacted with 8 grams of boric acid in 60 grams toluene solvent. The reaction solution was refluxed from 100° to 124° C. until water no longer azeotroped from the reaction (5.2 cc $H_2O$). The product mixture was filtered through diatomaceous earth to yield a clear amber liquid. This toluene solution of partially borated, partially phosphosulfurized glycerol monooleate was refluxed with 18 grams zinc oxide in 6 grams isopropanol at 95° C. for 6 hours. Toluene and isopropanol solvents were removed by vacuum distillation. The product was filtered through diatomaceous earth to yield a clear amber fluid.

Some of the metal salts of the partially borated, partially phosphosulfurized hydroxyl containing esters were blended into a fully formulated automotive engine oil (SAE 5W-20) containing detergent/dispersant, inhibitor package and tested on the Low Velocity Friction Apparatus (LVFA). Results are reported in Table 1. Friction was significantly reduced relative to the base oil. Reductions of up to 48% in the coefficient of friction were measured. Furthermore, all of the additives also had good copper corrosion inhibition. Most of the copper strip corrosion test results were 1A or 1B, see Table 3.

Low Velocity Friction Apparatus (LVFA)

The Low Velocity Friction Apparatus (LVFA) is used to measure the friction of test lubricants under various loads, temperatures, and sliding speeds. The LVFA consists of a flat SAE 1020 steel surface (diam. 1.5 in.) which is attached to a drive shaft and rotated over a stationary, raised, narrow ringed SAE 1020 steel surface (area 0.08 in.$^2$). Both surfaces were submerged in the test lubricant. Friction between the steel surfaces is measured using a torque arm strain gauge system. The strain gauge output, which is calibrated to be equal to the coefficient of friction, is fed to the Y axis of an X-Y plotter. The speed signal from the tachometer-generator is fed to the X-axis. To minimize external friction, the piston is supported by an air bearing. The normal force loading the rubbing surfaces is regulated by air pressure on the bottom of the piston. The drive system consists of an infintely variable-speed hydraulic transmission driven by a ½ HP electric motor. To vary the sliding speed, the output speed of the transmission is regulated by a lever cam-motor arrangement.

Procedure

The rubbing surfaces and 12–13 ml. of test lubricant are placed on the LVFA. A 500 psi load is applied, and the sliding speed is maintained at 40 fpm at ambient temperature for a few minutes. A plot of coefficients of friction ($U_k$) over a range of sliding speeds, 5 to 40 fpm (25–195 rpm), is obtained. A minimum of three measurements is obtained for each test lubricant. Then, the test lubricant and specimens are heated to 250° F., another set of measurements is obtained, and the system is run for 50 minutes at 250° F., 500 psi, and 40 fpm sliding speed. Freshly polished steel specimens are used for each run. The surface of the steel is parallel ground to 6 to 8 microinches. The percentages by weight are percentages by weight of the total lubricating oil composition, including the usual additive package. The data are percent decrease in friction according to:

$$\frac{(U_k \text{ of oil alone}) - (U_k \text{ of Additive plus oil})}{(U_k \text{ of oil alone})} \times 100$$

Thus, the corresponding value for the oil alone would be zero for the form of the data used in Table 1 below.

TABLE 1

Friction Characteristics

| Base Oil Plus Example No. | Additive Conc., Wt. % | Reduction or % Change in Coefficient of Friction | |
|---|---|---|---|
| | | 5 Ft./Min. | 30 Ft./Min. |
| Example 1 | | | |
| Base Oil only (fully formulated SAE 5W-20 automotive engine oil), no additive | — | 0 | 0 |
| Example 3 | | | |
| Zinc salt of partially phosphosulfurized glycerol monooleate | 4 | 18 | 14 |
| Example 4 | | | |
| Partially borated zinc salt of partially phosphosulfurized glycerol monooleate | 4 | 29 | 20 |
| Example 5 | | | |
| Zinc salt of borated, partially phosphosulfurized glycerol monooleate | 4 | 48 | 35 |
| Example 7 | | | |
| Zinc salt of partially phosphosulfurized glycerol monooleate | 4 | 18 | 8 |
| Example 8 | | | |
| Partially borated zinc salt of partially phosphosulfurized glycerol monooleate | 4 | 34 | 20 |
| Example 9 | | | |
| Zinc salt of partially borated, partially phosphosulfurized glycerol monooleate | 4 | 40 | 32 |

Certain of the examples were also tested for their antioxidation characteristics in the B-10 Catalytic Oxidation Test at 325° F. for 40 hours. The test lubricant composition is subjected to a stream of air which is bubbled through the composition at a rate of 5 liters per hour at 325° F. for 40 hours. Present in the composition comprising a 200 seconds paraffinic neutral oil in addition to the additive compound were metals commonly used as materials to construct engines namely:

(a) 15.6 sq. in. of sand-blasted iron wire;
(b) 0.78 sq. in. of polished copper wire;
(c) 0.87 sq. in. of polished aluminum wire; and
(d) 0.107 sq. in. of polished lead surface.

The test results are reported below in Table 2.

TABLE 2

Catalytic Oxidation Test 40 Hours @ 325° F.

| Base Oil Plus Example No. | Additive Conc., Wt. % | Lead Loss, Mg | % Increase in Viscosity of Oxidized Oil Using KV @ 210° F. | Neut. Number NN |
|---|---|---|---|---|
| Base Oil only, 0% Additive 200" Solvent Paraffinic Neutral Lubricating Oil | — | −1.2 | 67 | 3.62 |
| Example 3 | | | | |
| Zinc salt of partially phosphosulfurized glycerol monooleate | 1 | 1.9 | 10 | 2.4 |
| | 3 | — | 14 | 3.3 |
| Example 4 | | | | |
| Partially borated zinc salt of partially phosphosulfurized glycerol monooleate | 1 | 1.4 | 43 | 2.52 |
| | 3 | — | 14 | 2.03 |
| Example 5 | | | | |
| Zinc salt of borated, partially phosphosulfurized glycerol monooleate | 1 | 0.6 | | |
| | 3 | — | | |
| Example 7 | | | | |
| Zinc salt of partially phosphosulfurized glycerol monooleate | 1 | 1.7 | 12 | 3.3 |
| | 3 | — | 24 | 5.3 |
| Example 8 | | | | |
| Partially borated zinc salt of partially phosphosulfurized glycerol monooleate | 1 | 2.2 | 34 | 2.92 |
| | 3 | — | 16 | 1.59 |
| Example 9 | | | | |
| Zinc salt of partially borated partially phosphosulfurized glycerol monooleate | 1 | 0.0 | 45 | 3.05 |
| | 3 | — | 11 | 1.22 |

Corrosion inhibiting properties of representative compounds prepared above were also tested in 200" solvent parafinic neutral lubricating oil via copper corrosivity tests, ASTM D 130-6, ASTM D 130-9. The results are reported in Table 3, below.

TABLE 3

Copper Strip Corrosivity Characteristics

| Base Oil Plus Example No. | Concentration in 200" SPN | ASTM D130-6 250° F./3 Hrs | ASTM D130-9 210° F./6 Hrs |
|---|---|---|---|
| Example 3 | | | |
| Zinc salt of partially phosphosulfurized glycerol monooleate | 1 | 1A | 1A |
| Example 4 | | | |
| Partially borated zinc salt of partially phosphosulfurized glycerol monooleate | 1 | 1A | 1A |
| | 3 | 1A | 1A |
| Example 5 | | | |
| Zinc salt of borated, partially phosphosulfurized glycerol monooleate | 3 | 1B | 1B |
| Example 7 | | | |

TABLE 3-continued

Copper Strip Corrosivity Characteristics

| Base Oil Plus Example No. | Concentration in 200° SPN | ASTM D130-6 250° F./3 Hrs | ASTM D130-9 210° F./6 Hrs |
|---|---|---|---|
| Zinc salt of partially phosphosulfurized glycerol monooleate Example 8 | 1 | 1A | 1A |
|  | 3 | 1A | 1A |
| Partially borated zinc salt of partially phosphosulfurized glycerol monooleate Example 9 | 1 | 1A | 1A |
|  | 3 | 1B | 1A |
| Zinc salt of partially borated, partially phosphosulfurized glycerol monooleate | 1 | 2B | 1B |
|  | 3 | 2B | 1B |

It will be noted that the metal salts of the partially phosphosulfurized, partially borated polyol-derived hydroxyesters reduce friction, reduce wear, and inhibit corrosion and inhibit oxidation when formulated into a variety of oleagenous lubricant materials. Furthermore, in keeping with the fact that some automotive engine oils are presently limited to 0.1 to 0.13 weight percent phosphorus, the compositions in accordance herewith contain extremely small amounts of phosphorus.

Although the present invention has been described with preferred embodiments, it is to be understood that modifications and variations may be resorted to without departing from the spirit and scope of this invention, as those skilled in the art will readily understand. Such variations and modifications are considered to be within the purview and scope of the appended claims.

We claim:

1. A lubricant composition comprising a major proportion of an oil of lubricating viscosity or grease or other solid lubricant prepared therefrom and a minor effective amount of a multifunctional additive consisting of the metal salt of a partially borated, partially phosphosulfurized hydroxyl-containing ester derived from a polyol.

2. The composition of claim 1 wherein the hydroxyl-containing ester is selected from the group consisting of

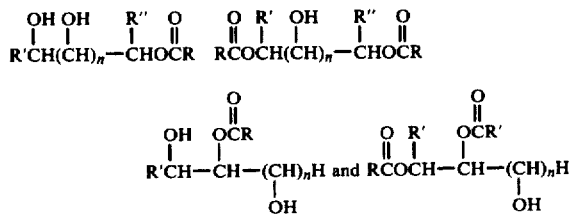

wherein $R = C_8-C_{30}$, and is saturated or unsaturated, straight chain or branched, cyclic hydrocarbyl, alkylaryl, arylalkyl; $R'$ and $R''$ can be H or $C_1$ to $C_{10}$ hydrocarbyl and $n = 1$ to 4 and where the hydroxyl-containing esters are mono- or diesters prepared from the reaction of polyols selected from glycerol, sorbitol, or sorbitan or related polyols with organic acids having from 8 to 30 carbon atoms such as RCOOH selected from the group consisting of lauric, myristic, palmitic, stearic, oleic, linoleic, or linolenic or mixtures thereof and wherein the metal is selected from the group consisting of zinc, nickel, cobalt, iron, silver and molybdenum.

3. The composition of claim 2 wherein the additive is a zinc salt.

4. The composition of claim 3 wherein the additive is a zinc salt of borated, partially phosphosulfurized glycerol monooleate.

5. The composition of claim 3 wherein the additive is a partially borated zinc salt of partially phosphosulfurized glycerol monooleate.

6. The composition of claim 1 wherein said oil of lubricating viscosity is selected from mineral oils, or fractions thereof, synthetic oils or mixtures of mineral and synthetic oils.

7. The composition of claim 6 wherein said oil is selected from mineral oils, synthetic oils or mixtures thereof.

8. The composition of claim 7 wherein said oil is mineral oil.

9. The composition of claim 7 wherein said oil is a synthetic oil.

10. The composition of claim 1 wherein said major proportion is a grease or other solid lubricant.

11. An additive compound consisting of a metal salt of a partially borated, partially phosphosulfurized hydroxyl-containing ester derived from a polyol wherein the hydroxyl-containing ester is selected from the group consisting of

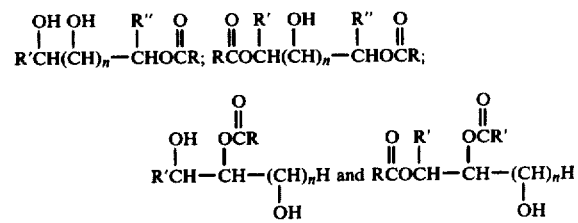

where $R = C_8-C_{30}$, and is saturated or unsaturated straight chain or branched, cyclic hydrocarbyl, alkylaryl, arylalkyl; $R'$ and $R''$ can be H or $C_1-C_{10}$ hydrocarbyl and $n = 1$ to 4 and where the hydroxyl-containing esters are mono- and diesters prepared from the reaction of polyols selected from glycerol, sorbitol, or sorbitan or related polyols with acids selected from lauric, myristic, palmitic, stearic, oleic, linoleic, or linolenic or mixtures thereof and wherein the metal is selected from the group consisting of zinc, nickel, cobalt, iron, silver and molybdenum.

12. The additive compound of claim 11 wherein said compound is a zinc salt.

13. The additive compound of claim 12 wherein said compound is a partially borated zinc salt of partially phosphosulfurized glycerol monooleate.

14. The additive compound of claim 12 wherein said compound is a zinc salt of borated partially phosphosulfurized glycerol monooleate.

15. A method for increasing the fuel consumption of internal combustion engines comprising treating the moving parts of said engines with a lubricant composition as described in claim 1.

* * * * *